United States Patent
Torai et al.

(10) Patent No.: US 12,325,851 B2
(45) Date of Patent: Jun. 10, 2025

(54) STIRRING DEVICE AND PREPROCESSING DEVICE

(71) Applicants: NATIONAL UNIVERSITY CORPORATION KOBE UNIVERSITY, Kobe (JP); SHIMADZU CORPORATION, Kyoto (JP)

(72) Inventors: Aya Torai, Kyoto (JP); Yoshihiro Matsumoto, Kyoto (JP); Tomohisa Hasunuma, Kobe (JP)

(73) Assignees: NATIONAL UNIVERSITY CORPORATION KOBE UNIVERSITY, Kobe (JP); SHIMADZU CORPORATION, Kyoto (JP)

(*) Notice: Subject to any disclaimer, the term of this patent is extended or adjusted under 35 U.S.C. 154(b) by 1180 days.

(21) Appl. No.: 17/259,620

(22) PCT Filed: Jul. 10, 2019

(86) PCT No.: PCT/JP2019/027326
§ 371 (c)(1),
(2) Date: Jan. 12, 2021

(87) PCT Pub. No.: WO2020/017410
PCT Pub. Date: Jan. 23, 2020

(65) Prior Publication Data
US 2021/0292705 A1 Sep. 23, 2021

(30) Foreign Application Priority Data
Jul. 17, 2018 (JP) .................................. 2018-134177

(51) Int. Cl.
C12M 1/00 (2006.01)
C12M 1/06 (2006.01)
(Continued)

(52) U.S. Cl.
CPC ............ *C12M 47/02* (2013.01); *C12M 27/02* (2013.01); *C12M 41/36* (2013.01); *C12M 41/48* (2013.01); *G01N 21/251* (2013.01)

(58) Field of Classification Search
CPC ...... C12M 33/00; C12M 41/36; C12M 41/48; C12M 47/04; G01N 1/00;
(Continued)

(56) References Cited

U.S. PATENT DOCUMENTS

| 3,061,280 A | 10/1962 | Kraft et al. |
| 2012/0252110 A1 | 10/2012 | Oura et al. |
| 2018/0127695 A1* | 5/2018 | Nam ...................... G01N 35/04 |

FOREIGN PATENT DOCUMENTS

JP 2012-200239 A 10/2012

OTHER PUBLICATIONS

International Search Report for PCT/JP2019/027326 dated Sep. 17, 2019 (PCT/ISA/210).
(Continued)

*Primary Examiner* — Lydia Edwards
(74) *Attorney, Agent, or Firm* — Sughrue Mion, PLLC (57) ABSTRACT

When a stirring device 11 performs processing of stirring a mixed solution in a test tube S, a holding mechanism 13 and a movement mechanism 14 are operated so that the test tube S is moved to a position of B2. Then, in the test tube S, the cells attached to the inner surface of the test tube S and the liquid are separated. Further, the cells attached to the inner surface of the test tube S are detected by a color sensor 152. Therefore, it is possible to reduce the work for determining the end of the stirring processing by the user. As a result, the workability of the user when using the stirring device 11 can be improved.

3 Claims, 7 Drawing Sheets

(51) Int. Cl.
*C12M 1/34* (2006.01)
*C12M 1/36* (2006.01)
*G01N 21/25* (2006.01)

(58) Field of Classification Search
CPC .... G01N 2001/002; G06T 2207/30242; G06T 2207/30024; G06V 20/69
See application file for complete search history.

(56) References Cited

OTHER PUBLICATIONS

Written Opinion for PCT/JP2019/027326 dated Sep. 17, 2019 (PCT/ISA/237).

* cited by examiner

STIRRING DEVICE AND PREPROCESSING DEVICE

CROSS REFERENCE TO RELATED APPLICATIONS

This application is a National Stage of International Application No. PCT/JP2019/027326 filed Jul. 10, 2019, claiming priority based on Japanese Patent Application No. 2018-134177 filed Jul. 17, 2018.

TECHNICAL FIELD

The present invention relates to a stirring device for stirring a mixed solution in which a reagent is mixed with cells.

BACKGROUND ART

A technology has been known in which an analysis such as metabolome analysis is performed by culturing cells of microorganisms and plants in a culture medium in a culture vessel, collecting cells from the culture medium, performing pre-processing, and then supplying the cells to a liquid chromatograph mass spectrometer. In this kind of technology, a sampling apparatus for sampling a culture medium containing cells and a pre-processing apparatus for performing pre-processing on the cells contained in the sampled culture medium are used. The sampling of the culture medium is performed under an aseptic condition (refer to, for example, Patent Document 1 below).

In the pre-processing apparatus, for example, centrifugation of the culture medium, removal of the liquid other than the cells after the centrifugation, supply of a reagent to the cells, stirring of the mixed solution containing the cells and the reagent, and the like are sequentially performed. Among these, the stirring of the mixed solution is performed by, for example, a dedicated stirring device.

As the stirring device, a device for performing the stirring by moving a test tube at a high speed in a state where the test tube in which the mixed solution is housed is held, is used. Such a device includes a motor, and a holding mechanism that holds the test tube at a position away from a drive shaft of the motor (position eccentric from the drive shaft). Then, the driving force from the motor is applied to the holding mechanism, so that the test tube held by the holding mechanism is moved at a high speed.

PRIOR ART DOCUMENT

Patent Documents

Patent Document 1: Japanese Patent Laid-Open No. 2012-200239

SUMMARY OF THE INVENTION

Problems to be Solved by the Invention

In the related art, in a case where the above-described stirring device is used, it has been determined by the user's visual observation whether or not the stirring of the mixed solution is ended. Specifically, the test tube was taken out of the holding mechanism, and the user visually checked the contents of the test tube to determine whether to end or continue the stirring processing. Therefore, there is a problem that the user's work when using the stirring device becomes complicated.

The invention has been made in view of the above circumstances, and an object of the invention is to provide a stirring device and a pre-processing apparatus which can improve workability of a user.

Means for Solving the Problems (1) A stirring device according to the invention is a stirring device for stirring a mixed solution in which a reagent is mixed with cells. The stirring device includes a stirring mechanism, a solid-liquid separation mechanism, and a cell detection mechanism. The stirring mechanism stirs the mixed solution in a container in which the mixed solution is housed. The solid-liquid separation mechanism separates the cells attached to the container from liquid other than the cells in the container after the stirring by the stirring mechanism. The cell detection mechanism detects whether or not the cells separated from the liquid by the solid-liquid separation mechanism are attached to the container.

According to such a configuration, in the stirring device, when the mixed solution is stirred by the stirring mechanism, the cells attached to the container and the liquid other than the cells are separated by the solid-liquid separation mechanism. Then, whether or not there are cells attached to the container is detected by the cell detection mechanism.

Therefore, when the stirring processing is ended according to the detection by the cell detection mechanism that no cells are attached to the container, the stirring processing can be ended at an appropriate timing.

As a result, it is possible to reduce the work for determining the end of the stirring processing by the user.

Therefore, the workability of the user when using the stirring device can be improved.

(2) The solid-liquid separation mechanism may rotate the container to separate the liquid other than the cells, from the cells attached to the container by gravity.

According to such a configuration, the cells attached to the container and the liquid other than the cells can be separated with a simple configuration.

(3) The stirring device may further include a control unit. The control unit causes the stirring mechanism to execute the stirring again in a case where the cell detection mechanism detects that the cells are attached to the container.

According to such a configuration, in the stirring device, the stirring processing can be automatically performed until the cells are not attached to the container.

Therefore, the workability of the user when using the stirring device can be improved.

(4) The cell detection mechanism may have a color sensor that detects the cells by color.

According to such a configuration, the cells attached to the container can be accurately detected by the cell detection mechanism.

(5) A pre-processing apparatus according to the invention is a pre-processing apparatus for performing pre-processing on cells. The pre-processing apparatus includes a centrifugation mechanism, a liquid removal mechanism, a reagent supply mechanism, and the stirring device. The centrifugation mechanism centrifuges a container in which a culture medium containing the cells is housed. The liquid removal mechanism removes liquid other than the cells centrifuged in the container by the centrifugation mechanism. The reagent supply mechanism generates a mixed solution by mixing a reagent with the cells in the container after the liquid is removed by the liquid removal mechanism. The stirring device stirs the mixed solution generated by the reagent supply mechanism.

According to such a configuration, the workability of the user can be improved in the pre-processing apparatus.

Effects of the Invention

According to the invention, in the stirring device, when the mixed solution is stirred by the stirring mechanism, the cells attached to the container and the liquid other than the cells are separated by the solid-liquid separation mechanism. Then, whether or not there are cells attached to the container is detected by the cell detection mechanism. Therefore, when the stirring processing is ended according to the detection by the cell detection mechanism that no cells are attached to the container, the stirring processing can be ended at an appropriate timing. As a result, it is possible to reduce the work for determining the end of the stirring processing by the user. Therefore, the workability of the user when using the stirring device can be improved.

MODE FOR CARRYING OUT THE INVENTION

1. Schematic Configuration of Automatic Pre-Processing System

Figure 1:
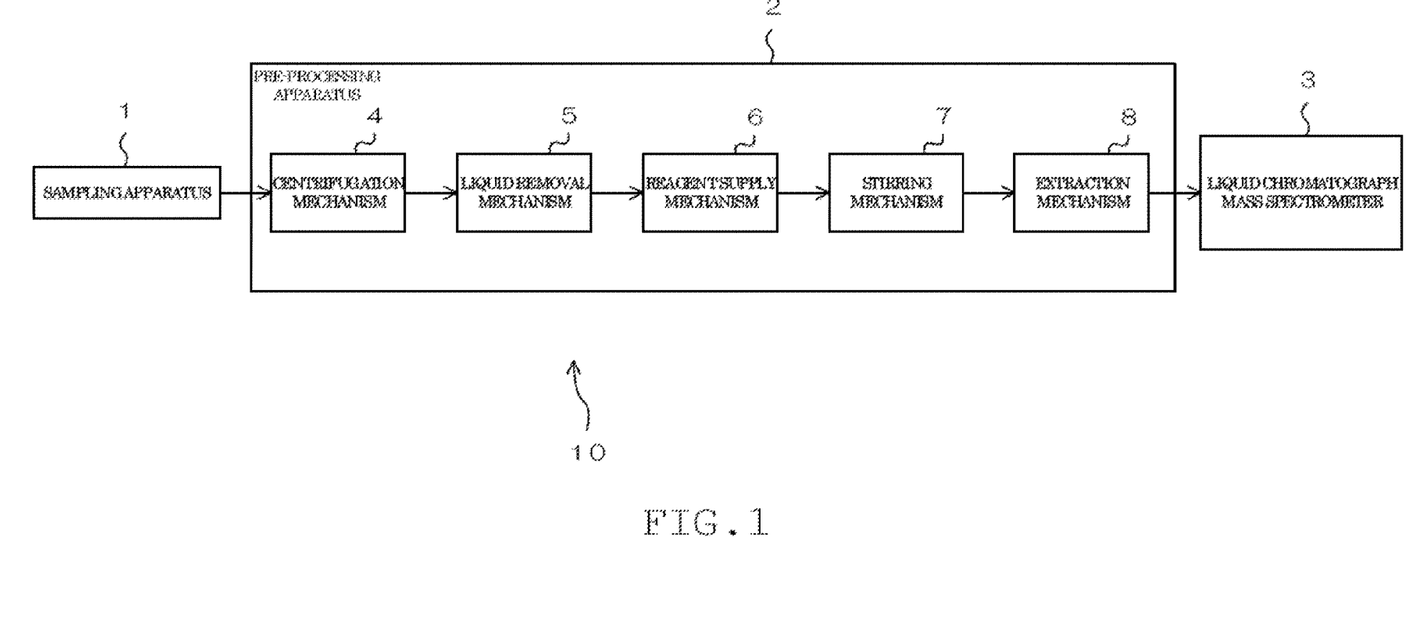
FIG. 1 is a block diagram illustrating a schematic configuration of an automatic pre-processing system including a pre-processing apparatus according to an embodiment of the invention.

FIG. 1 is a block diagram illustrating a schematic configuration of an automatic pre-processing system 10 including a pre-processing apparatus according to an embodiment of the invention. The automatic pre-processing system 10 is a device for automatically performing pre-processing on an analysis target. In the present embodiment, the analysis target is, for example, a cultured cell, and more specifically, a bacterial cell.

The automatic pre-processing system 10 includes the sampling apparatus 1 and a pre-processing apparatus 2. The metabolites of the cells are extracted from the cells after the pre-processing is performed by the automatic pre-processing system 10, and are supplied to a liquid chromatograph mass spectrometer 3. The liquid chromatograph mass spectrometer 3 is only an example of an analysis device for analyzing an analysis target, and it is also possible to perform an analysis by using another analysis device.

The sampling apparatus 1 is a apparatus for sampling a liquid from a container (culture container). For example, the cells of microorganisms and plants are cultured in a culture medium in a container called a bioreactor, and the culture medium containing the cells in the bioreactor is sampled by the sampling apparatus 1. In the bioreactor, for example, a stirring member that is rotated by using magnetic force, an oxygen concentration sensor for detecting the concentration of dissolved oxygen, and the like are provided, and the cells are cultured in the sampling apparatus 1 by adjusting the dissolved oxygen concentration while stirring the culture medium in the bioreactor.

The pre-processing apparatus 2 performs pre-processing on the cells contained in the culture medium sampled from the bioreactor. In the sampling apparatus 1, the culture medium containing the cells is housed in a test tube as a container (sampling container). The pre-processing apparatus 2 is provided with a centrifugation mechanism 4, a liquid removal mechanism 5, a reagent supply mechanism 6, a stirring mechanism 7, an extraction mechanism 8, and the like, and by each of these mechanisms, the pre-processing is sequentially performed on the cells contained in the culture medium in the test tube.

The centrifugation mechanism 4 centrifuges the test tube in which the culture medium containing the cells is housed. As a result, centrifugal force is applied to the culture medium in the test tube, and the cells (solid) and the liquid other than the cells are separated. Then, the liquid other than the cells centrifuged in the test tube by the centrifugation mechanism 4 is removed by using the liquid removal mechanism 5, and thereby the cells are collected.

The reagent is supplied by the reagent supply mechanism 6, to the test tube after the liquid is removed by the liquid removal mechanism 5. As a result, the reagent is mixed with the cells in the test tube, and a mixed solution is generated. Then, the mixed solution generated by the reagent supply mechanism 6 is stirred by the stirring mechanism 7.

The reagent used in the present embodiment is a reagent for extracting metabolites in the cells, and a suspension in which the metabolites are extracted from the cells is obtained by stirring the mixed solution in which the reagent is mixed with the cells. A part of the suspension obtained in this manner is extracted as an extraction liquid by the extraction mechanism 8, and is supplied to the liquid chromatograph mass spectrometer 3.

2. Detailed Configuration of Stirring Device

Figure 2:
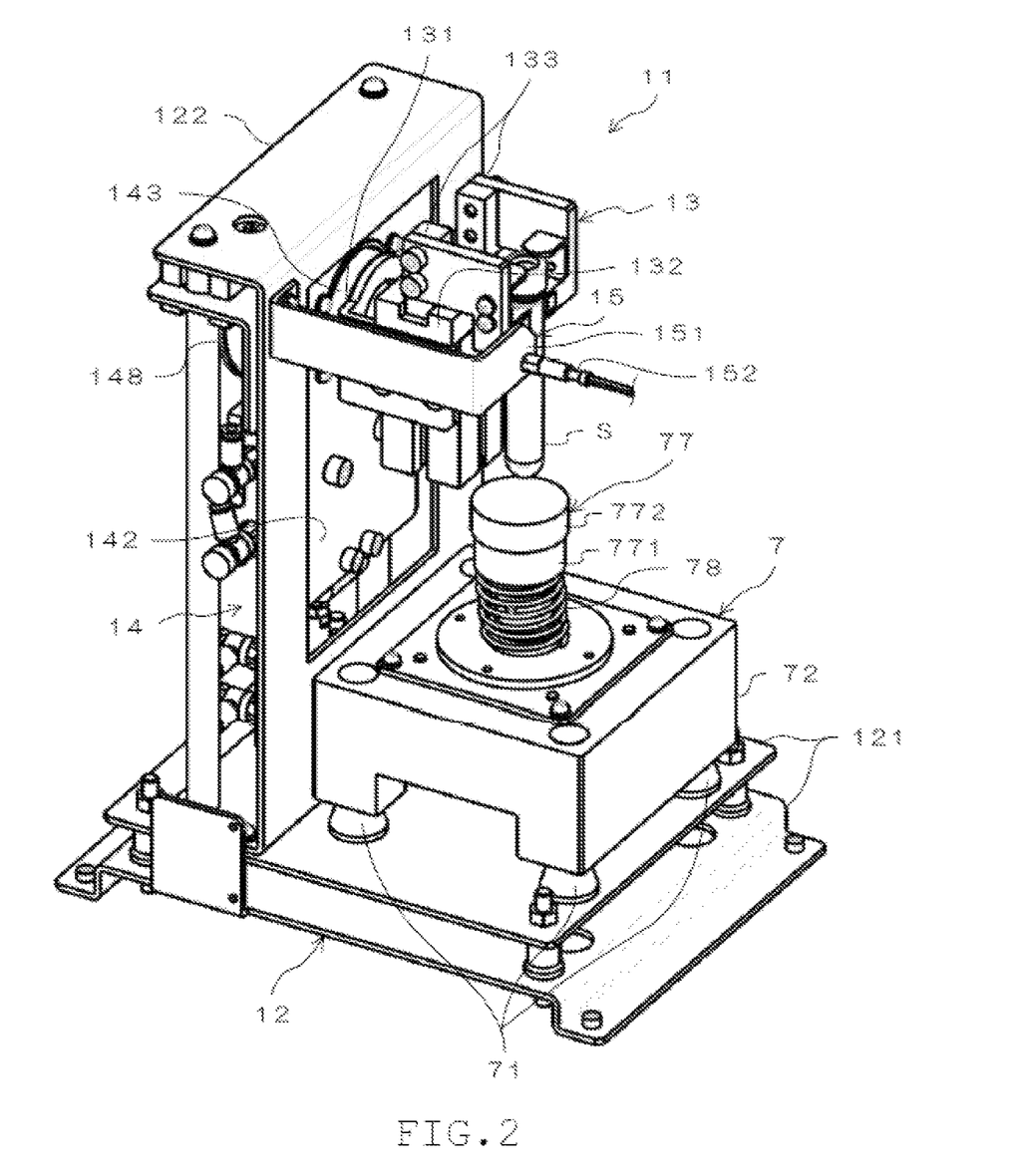
FIG. 2 is a perspective view illustrating a configuration of a stirring device according to the embodiment of the invention.
Figure 3:
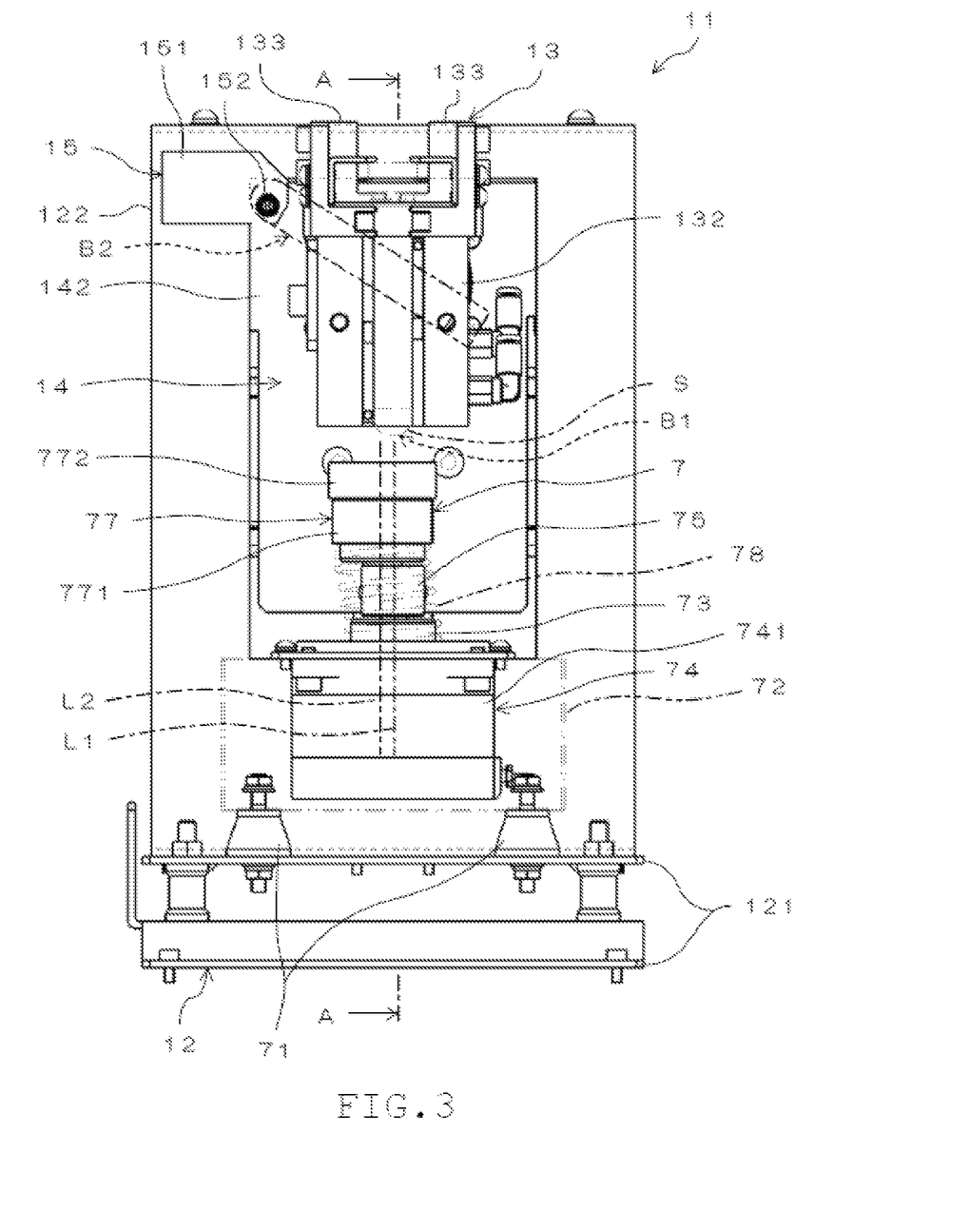
FIG. 3 is a front view of the stirring device of FIG. 2.
Figure 4:
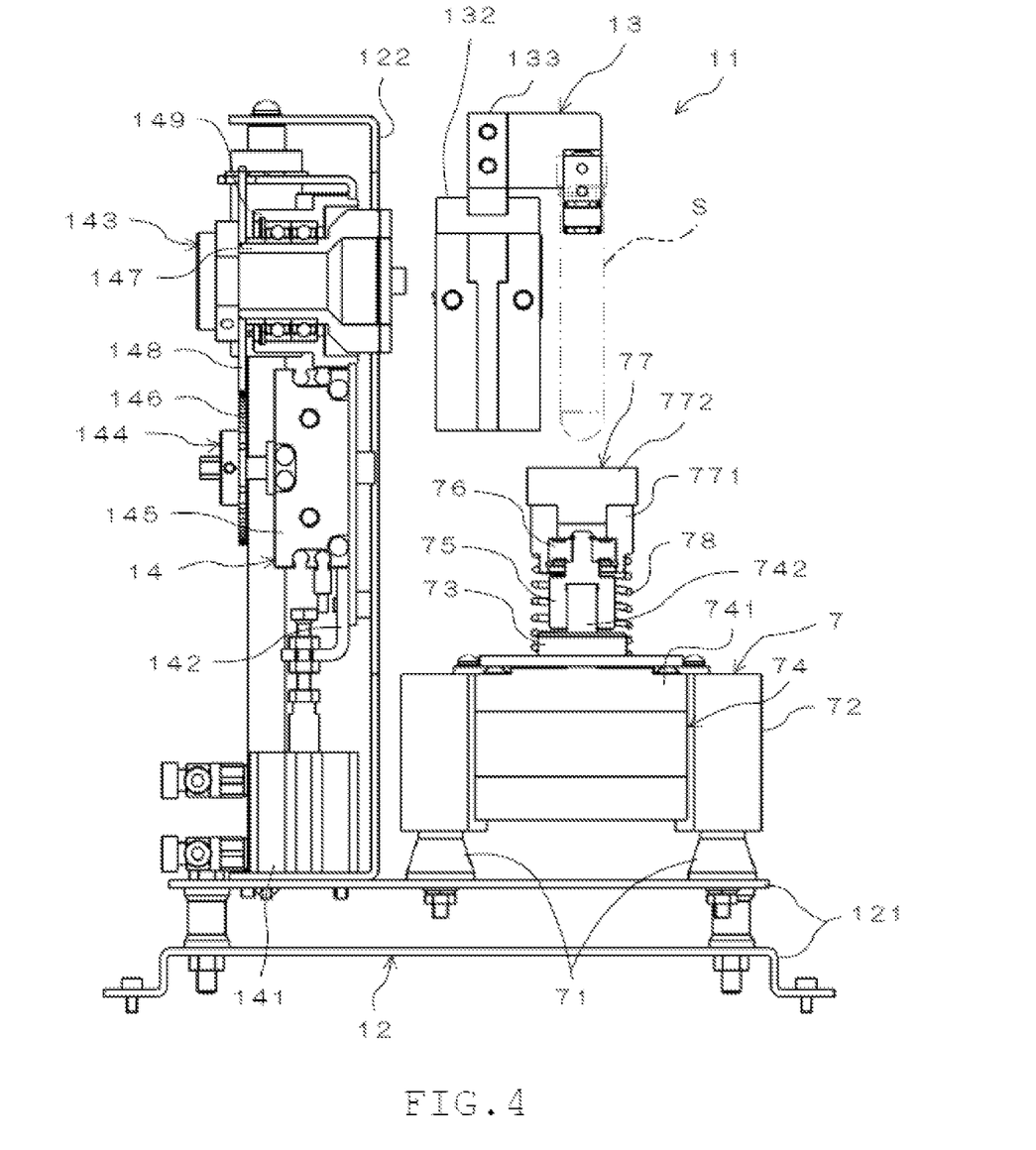
FIG. 4 is a sectional view taken along the line A-A of FIG. 3.
Figure 5:
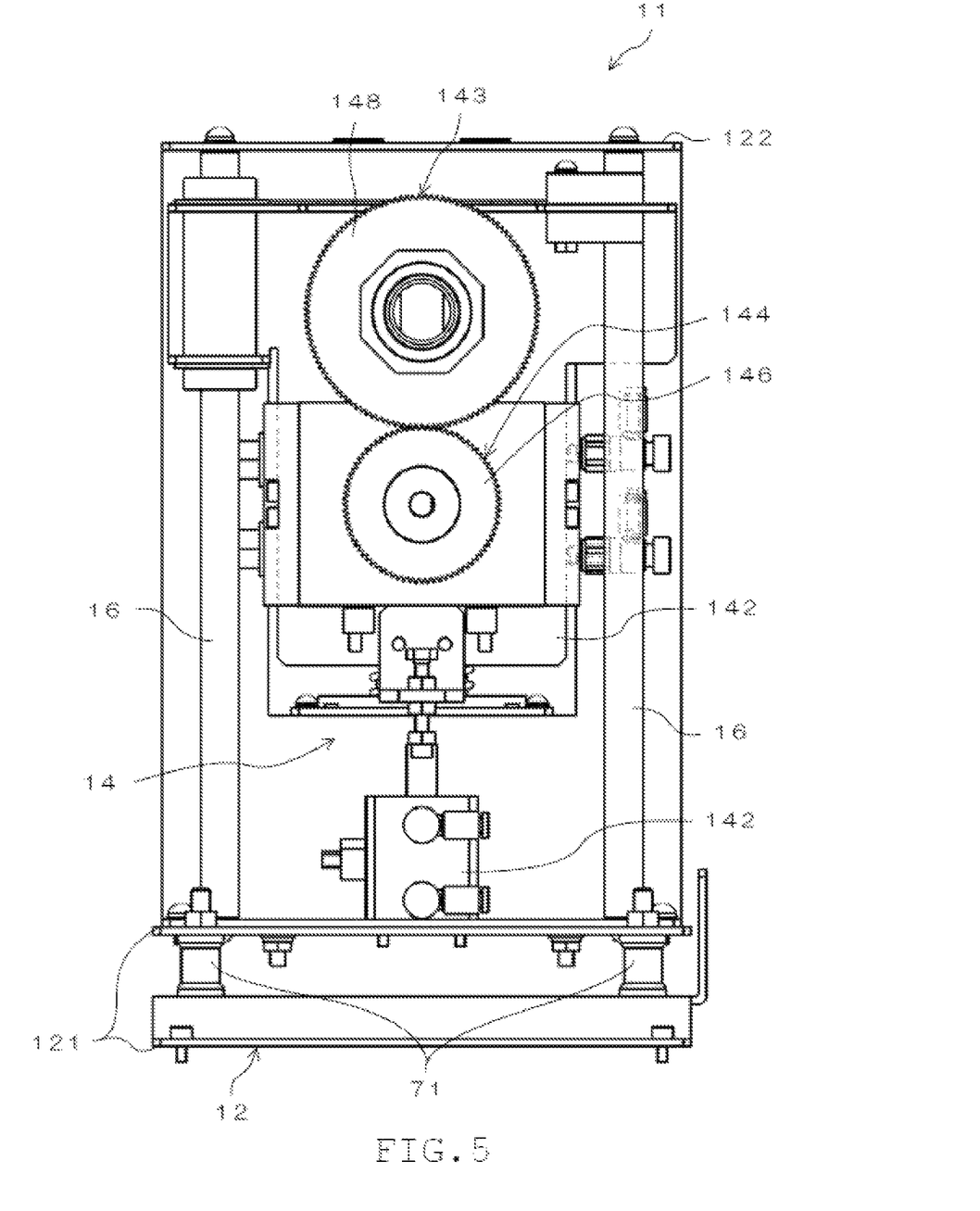
FIG. 5 is a rear view of the stirring device of FIG. 2.
Figure 6:
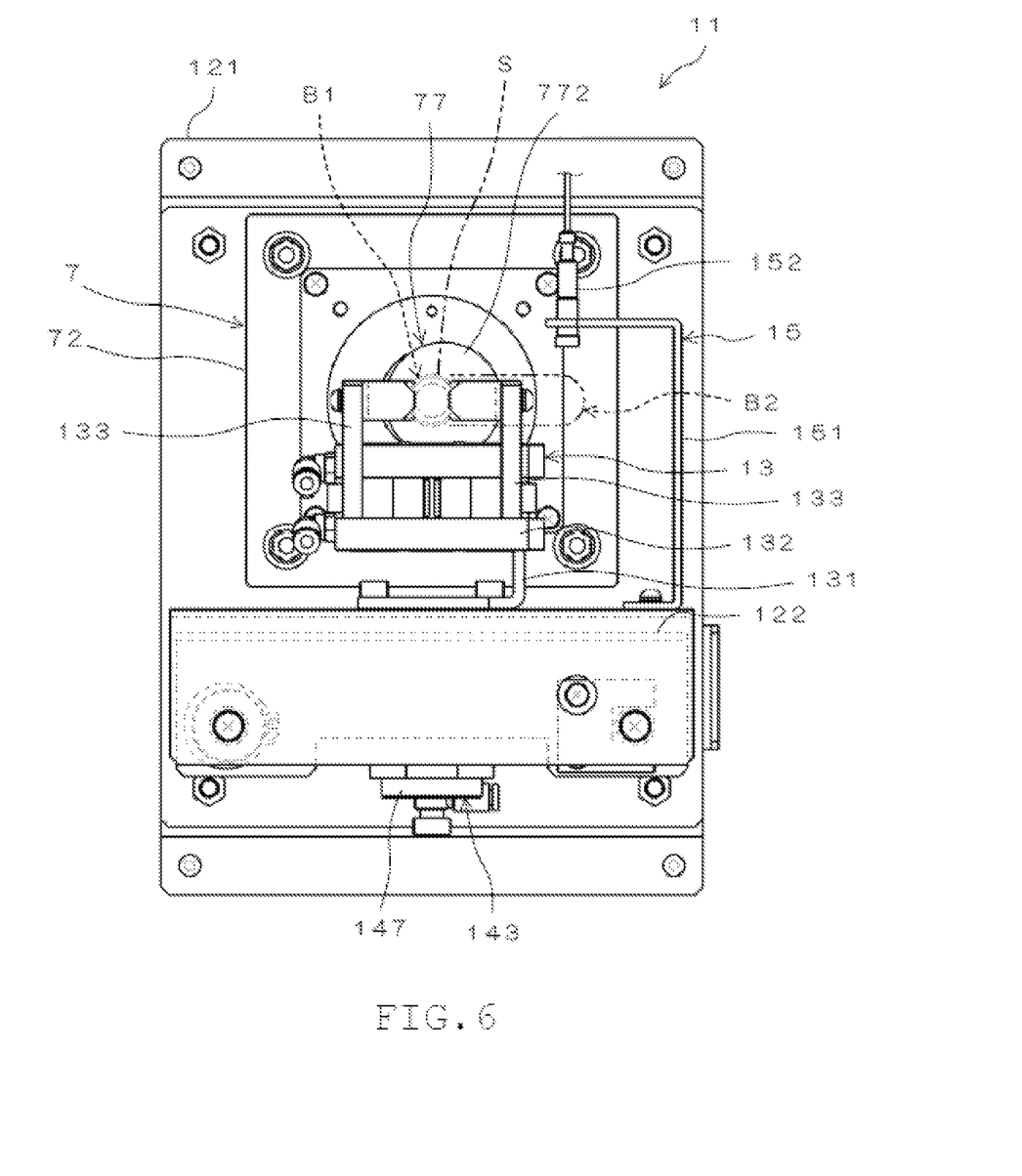
FIG. 6 is a plan view of the stirring device of FIG. 2.

FIG. 2 is a perspective view illustrating a configuration of a stirring device 11 according to the embodiment of the invention. FIG. 3 is a front view of the stirring device 11. FIG. 4 is a sectional view taken along the line A-A of FIG. 3. FIG. 5 is a rear view of the stirring device 11. FIG. 6 is a plan view of the stirring device 11.

The stirring device 11 is provided in the pre-processing apparatus 2 described above. The stirring device 11 includes a frame 12, the above-described stirring mechanism 7, a holding mechanism 13, a movement mechanism 14, and a cell detection mechanism 15.

As illustrated in FIGS. 2 and 4, the frame 12 is formed in an L shape in a side view, and is made of a metal material. The frame 12 includes a horizontal frame 121 and a vertical frame 122. The horizontal frame 121 is formed in a plate shape, and extends along a horizontal plane. The horizontal frame 121 is fixed to an installation surface (not illustrated). The vertical frame 122 is fixed to the upper surface of the horizontal frame 121. The vertical frame 122 is formed in a plate shape, and extends upward from one end portion of the horizontal frame 121 (left end portion in FIGS. 2 and 4).

The stirring mechanism 7 is fixed on the horizontal frame 121. The stirring mechanism 7 includes a plurality of (four)

leg portions 71, a housing 72, a base portion 73, a motor 74, a rotation portion 75, a bearing 76, a pedestal portion 77, and a spring 78.

Each leg portion 71 is fixed to the upper surface of the horizontal frame 121. Each leg portion 71 is formed in a tapered shape that tapers upward. The plurality of (four) leg portions 71 are arranged to be spaced apart from each other.

The housing 72 is fixed on the leg portions 71. The housing 72 is formed in a hollow rectangular parallelepiped shape.

As illustrated in FIGS. 3 and 4, the base portion 73 is fixed to a central portion of the upper surface of the housing 72. The base portion 73 is formed in a cylindrical shape.

The motor 74 is fixed to the housing 72. The motor 74 includes a motor body 741 and a rotation shaft 742. The motor body 741 is fixed in the housing 72. The rotation shaft 742 extends upward from the motor body 741. The rotation shaft 742 is inserted into an opening (not illustrated) formed on the upper surface of the housing 72 and an internal space of the base portion 73. The tip end portion of the rotation shaft 742 is arranged above the housing 72.

The rotation portion 75 is fixed to the rotation shaft 742. The rotation portion 75 is formed in a substantially columnar shape. The rotation portion 75 is formed such that the diameter of the upper portion is small and the diameter of the lower portion is large. A recess that is recessed upward is formed in the lower portion of the rotation portion 75. The rotation shaft 742 of the motor 74 is inserted into the recess of the rotation portion 75.

The bearing 76 is placed on the upper end portion of the rotation portion 75. That is, the upper end portion of the rotation portion 75 is inserted into the internal space of the bearing 76. A part of the inner surface of the bearing 76 is in contact with the peripheral surface of the upper end portion of the rotation portion 75.

The pedestal portion 77 is fixed on the bearing 76. The pedestal portion 77 includes a tubular portion 771, and a plate portion 772.

The tubular portion 771 is formed in a cylindrical shape, and is fixed to the bearing 76. The tubular portion 771 covers the upper surface and the outer peripheral surface of the bearing 76.

The plate portion 772 is fixed to the upper end portion of the tubular portion 771. The plate portion 772 is formed in a disk shape, and is made of a rubber material. The central portion of the lower surface of the plate portion 772 protrudes downward. The lower end portion of the plate portion 772 (protrusion portion at the central portion of the lower surface) is fitted into the inside of the upper end portion of the tubular portion 771.

The spring 78 is a coil spring, and is arranged between the base portion 73 and the pedestal portion 77 (tubular portion 771). Specifically, the lower end portion of the spring 78 is fixed to the outer peripheral surface of the base portion 73, and the upper end portion of the spring 78 is fixed to the outer peripheral surface of the lower end portion of the tubular portion 771. The rotation shaft 742 of the motor 74 and the rotation portion 75 are arranged inside the spring 78.

In the stirring device 11, the bearing 76 and the pedestal portion 77 are provided at positions eccentric with respect to the rotation shaft 742 of the motor 74. Specifically, as illustrated in FIG. 3, an axis line L2 of the pedestal portion 77 (the bearing 76 and the pedestal portion 77) is deviated from an axis line L1 of the motor 74 (the rotation shaft 742) (is at a position where the axis line L2 does not match the axis line L1).

The holding mechanism 13 is a mechanism for holding a test tube S. The movement mechanism 14 is a mechanism for moving the holding mechanism 13. The movement mechanism 14 is fixed to the vertical frame 122. The holding mechanism 13 is connected to the movement mechanism 14.

As illustrated in FIGS. 4 and 5, the movement mechanism 14 includes an up-down cylinder 141, a main body portion 142, a rotation cylinder 144, a bearing 149, and a connection portion 143.

The up-down cylinder 141 is fixed to the lower end portion of the vertical frame 122. When air is supplied from an air supply unit 17 (described later), the up-down cylinder 141 moves the cylinder in the vertical direction.

The main body portion 142 is arranged above the up-down cylinder 141. The main body portion 142 constitutes a base part of the movement mechanism 14. The vertical frame 122 is provided with one pair of rods 16 extending in the vertical direction. The main body portion 142 is attached in a movable state with respect to the one pair of rods 16. The lower end portion of the main body portion 142 is connected to the up-down cylinder 141 (cylinder part in the up-down cylinder 141). The main body portion 142 is moved in the vertical direction together with the cylinder part of the up-down cylinder 141.

As illustrated in FIG. 4, the rotation cylinder 144 is attached to a central portion of the main body portion 142. The rotation cylinder 144 includes a cylinder body 145 and a gear 146. Air is supplied from the air supply unit 17 (described later) to the cylinder body 145. The gear 146 has a shape in which gear teeth are formed on the end portion of a columnar shaft. The shaft of the gear 146 is inserted into the cylinder body 145. In the rotation cylinder 144, the gear 146 is rotated when air is supplied to the cylinder body 145.

The bearing 149 is fixed to the upper end portion of the main body portion 142. The bearing 149 is formed in a cylindrical shape extending in the horizontal direction.

The connection portion 143 is inserted into the inside of the bearing 149. The connection portion 143 includes a rotation portion 147 and a gear 148. The rotation portion 147 is formed in a columnar shape extending in the horizontal direction. One end portion of the rotation portion 147 (right end portion in FIG. 4) protrudes inward (toward the stirring mechanism 7) from the vertical frame 122. The gear 148 is formed in a disk shape, and has gear teeth at the tip end portion. The gear 148 of the connection portion 143 meshes with the gear 146 of the rotation cylinder 144.

As illustrated in FIGS. 2 and 6, the holding mechanism 13 includes an arm portion 131, a main body portion 132, and one pair of grip portions 133.

The arm portion 131 is fixed to one end portion of the connection portion 143 (rotation portion 147) of the movement mechanism 14. The arm portion 131 is formed in a bent plate shape, and extends inward (toward the stirring mechanism 7) from the connection portion 143.

The main body portion 132 is formed in a substantially rectangular parallelepiped shape, and is fixed to the arm portion 131.

Each grip portion 133 is attached to an upper end portion of the main body portion 132. Each grip portion 133 is formed in a plate shape. The one pair of grip portions 133 faces each other in the horizontal direction. The one pair of grip portions 133 can be moved in the opposite direction along the upper surface of the main body portion 132. The grip portion 133 is moved when air is supplied from the air supply unit 17 (described later). Specifically, the test tube S is interposed between the one pair of grip portions 133 by the one pair of grip portions 133 being moved to approach each other in the opposite direction. Further, from this state, the interposed state of the test tube S is released by the one pair of grip portions 133 being moved to be separated from each other in the opposite direction. The holding mechanism 13 and the movement mechanism 14 constitute an example of a solid-liquid separation mechanism.

The cell detection mechanism 15 is fixed to the upper end portion of the vertical frame 122. The cell detection mechanism 15 includes a support arm 151 and a color sensor 152. The support arm 151 is formed in a bent plate shape, and extends inward (toward the stirring mechanism 7) from the vertical frame 122. The color sensor 152 is fixed to the tip end portion of the support arm 151. The color sensor 152 is arranged apart from the vertical frame 122 in the horizontal direction. The color sensor 152 is directed toward the vertical frame 122.

3. Electrical Configuration of Stirring Device

Figure 7:
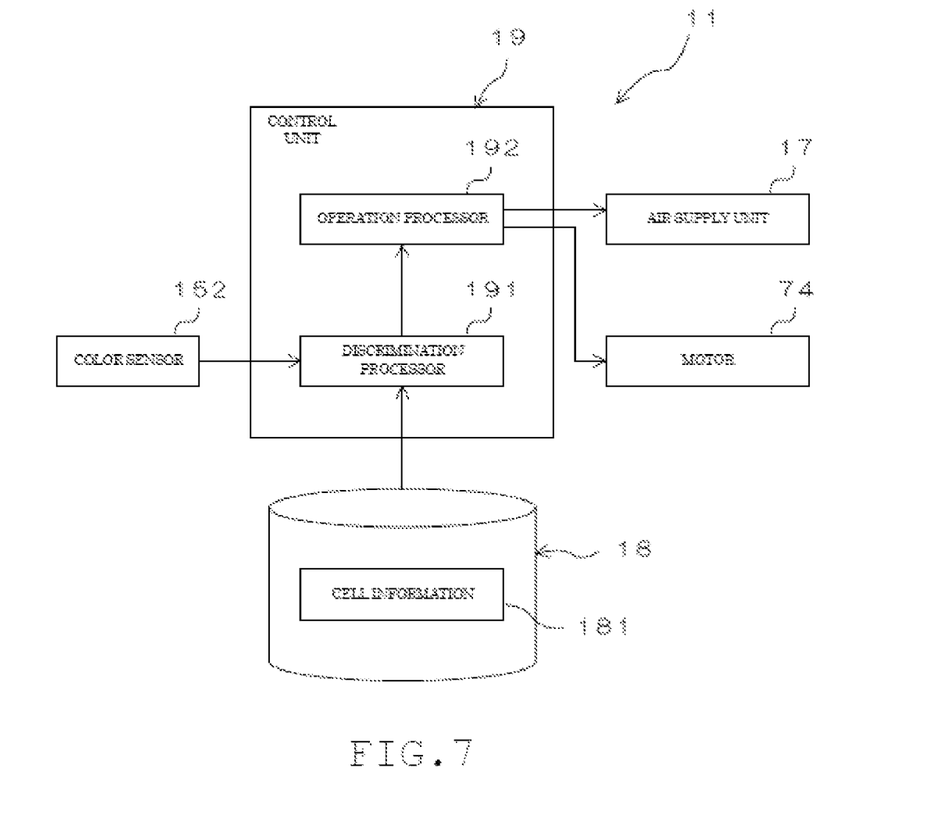
FIG. 7 is a block diagram illustrating an electrical configuration of the stirring device of FIG. 2.

FIG. 7 is a block diagram illustrating an electrical configuration of the stirring device 11.

The stirring device 11 includes, as the electrical configuration, the air supply unit 17, a storage unit 18, a control unit 19, and the like in addition to the motor 74 and the color sensor 152 described above.

The air supply unit 17 includes, for example, a cylinder and a valve. The air supply unit 17 supplies air to the grip portion 133, the up-down cylinder 141, and the rotation cylinder 144.

The storage unit 18 is composed of a read only memory (ROM), a random access memory (RAM), a hard disk, and the like. Cell information 181 is stored in the storage unit 18.

The cell information 181 is information regarding cells generated by stirring the mixed solution using the stirring device 11. In this example, the cell information 181 includes information on the color of the cell, specifically, information on the RGB value of the color of the cell.

The control unit 19 includes, for example, a central processing unit (CPU). The control unit 19 is electrically connected to the motor 74, the color sensor 152, the air supply unit 17, the storage unit 18, and the like. The control unit 19 functions as a discrimination processor 191, an operation processor 192, and the like by the CPU executing a control program.

The discrimination processor 191 performs processing of discriminating whether or not the stirring processing is completed on the basis of a detection signal from the color sensor 152 and the cell information 181 of the storage unit 18.

The operation processor 192 performs processing of controlling the operation of the air supply unit 17 and the motor 74 on the basis of the discrimination result of the discrimination processor 191.

4. Operation of Stirring Device

In the automatic pre-processing system 10, first, the culture medium containing the cells is introduced into the test tube S, and the centrifugation processing is performed on the test tube S. As a result, the culture medium in the test tube S is separated into the cells (solid) and the liquid other than the cells. Further, after the liquid in the test tube S is removed, the reagent is introduced into the test tube S. Then, the test tube S in this state is installed in the stirring device 11.

Specifically, as illustrated in FIG. 2, the test tube S is held by the holding mechanism 13 in a state where a cap is put on the upper end portion of the test tube S and the test tube S is along the vertical direction. At this time, the upper end portion of the test tube S is interposed by the grip portions 133 of the holding mechanism 13. When the test tube S is installed in the stirring device 11, as illustrated in FIGS. 3 and 4, the test tube S is located above the pedestal portion 77 of the stirring mechanism 7, and is spaced from the pedestal portion 77.

From this state, the operation processor 192 operates the air supply unit 17 such that the air supply unit 17 supplies air to the up-down cylinder 141 from one direction. As a result, the up-down cylinder 141 is operated downward, and thus the main body portion 142 and the connection portion 143 are moved downward. Then, the holding mechanism 13 is moved downward together with the connection portion 143.

Then, the bottom portion of the test tube S comes into contact with the upper surface of the pedestal portion 77 (plate portion 772). When the test tube S comes into contact with the plate portion 772, under the control of the operation processor 192, the operation of the up-down cylinder 141 is stopped, the movement of the main body portion 142 and the connection portion 143 is stopped, and the movement of the holding mechanism 13 is stopped. As a result, a state in which the bottom portion of the test tube S is in contact with the upper surface of the plate portion 772 is maintained.

In this state, the operation of the motor 74 is started under the control of the operation processor 192. As a result, the rotation shaft 742 of the motor 74 is rotated about the axis line L1. Then, the pedestal portion 77 and the bearing 76 are turned such that the axis line L2 is moved on the circumference of a circle centered on the axis line L1. At this time, the spring 78 is elastically deformed. In this way, the pedestal portion 77 is turned in accordance with the rotation of the motor 74.

When the pedestal portion 77 is turned in this way, the test tube S (the bottom portion of the test tube S) is moved at a high speed. As a result, the mixed solution in the test tube S is stirred. The cells are attached to the inner surface of the test tube S due to the centrifugation processing, but by performing the stirring processing in this way, the cells attached to the test tube S are appropriately peeled off from the test tube S.

Then, when a certain period of time elapses since the operation of the motor 74 is started, the operation of the motor 74 is stopped under the control of the operation processor 192.

After that, the operation processor 192 operates the air supply unit 17 such that the air supply unit 17 supplies air to the up-down cylinder 141 from the other direction. As a result, the up-down cylinder 141 is operated upward, and thus the main body portion 142 and the connection portion 143 are moved upward. Then, the holding mechanism 13 is moved upward together with the connection portion 143.

In FIG. 3, when the test tube S is moved up to a position indicated by B1, under the control of the operation processor 192, the operation of the up-down cylinder 141 is stopped, the movement of the main body portion 142 and the connection portion 143 is stopped, and the movement of the holding mechanism 13 is stopped. As a result, the test tube S is held at the position indicated by B1.

From this state, the operation processor 192 operates the air supply unit 17 such that the air supply unit 17 supplies air to the rotation cylinder 144 (cylinder body 145) from one direction. As a result, the gear 146 illustrated in FIG. 4 is rotated in one direction. Then, the gear 148 that meshes with the gear 146 is rotated in a direction opposite to the rotation direction of the gear 146. Further, the rotation portion 147 is rotated integrally with the gear 146.

As a result, the holding mechanism 13 is rotated together with the rotation portion 147. As illustrated in FIGS. 3 and 6, when the test tube S held by the holding mechanism 13 is moved up to a position indicated by B2, under the control of the operation processor 192, the operation of the rotation cylinder 144 is stopped, the rotation operation of the connection portion 143 is stopped, and the movement of the holding mechanism 13 is stopped. As a result, the test tube S is held at the position indicated by B2.

In a state where the test tube S is located at B2, the lower end portion of the test tube S is located above, the upper end portion of the test tube is located below, and the test tube S is inclined with respect to the vertical direction. Then, due to gravity, the liquid is separated from the cells attached to the inner surface of the test tube S (liquid is moved downward). In this state, when viewed in the horizontal direction, the lower end portion of the test tube S overlaps with the tip end portion of the color sensor 152.

The discrimination processor 191 reads out the cell information 181 of the storage unit 18. The discrimination processor 191 compares the information of the cell information 181 with the information obtained from the detection signal from the color sensor 152. In a case where the information obtained from the detection signal from the color sensor 152 is included in the cell information 181 or in a case where the information obtained from the detection signal from the color sensor 152 is close to the cell information 181, the discrimination processor 191 discriminates that the cells are attached to the inner surface of the test tube S. For example, in a case where the RGB value indicated by the detection signal from the color sensor 152 is included in the RGB value indicated by the cell information 181, the discrimination processor 191 discriminates that the cells are attached to the inner surface of the test tube S.

In a case where the discrimination processor 191 discriminates that the cells are attached to the inner surface of the test tube S, the stirring processing is executed again in the stirring device 11. Specifically, the operation processor 192 operates the air supply unit 17 such that the air supply unit 17 supplies air to the rotation cylinder 144 (cylinder body 145) from the other direction. As a result, the gear 146 illustrated in FIG. 4 is rotated in the other direction. Then, the gear 148 that meshes with the gear 146 is rotated in a direction opposite to the rotation direction of the gear 146. Further, the rotation portion 147 is rotated integrally with the gear 146, and the test tube S held by the holding mechanism 13 returns to the position indicated by B1.

From this state, the test tube S is moved downward to come into contact with the pedestal portion 77 in the same manner as the above-described operation. Further, the motor 74 is rotated so that the mixed solution in the test tube S is stirred again.

After that, the above-described operation is repeated. That is, the operation of detecting the cells attached to the inner surface of the test tube S and the operation of stirring the mixed solution in the test tube S are repeated.

Then, in a case where the discrimination processor 191 determines that the cells are not attached to the inner surface of the test tube S (case where the cells attached to the test tube S are not detected), the stirring processing in the stirring device 11 is completed after test tube S is moved to be located at B1.

When the stirring processing in the stirring device 11 is completed, the suspension in the test tube S is extracted by the extraction mechanism 8, and is supplied to the liquid chromatograph mass spectrometer 3 (refer to FIG. 1).

5. Effects (1) In the present embodiment, when the stirring device 11 performs the processing of stirring the mixed solution in the test tube S, the holding mechanism 13 and the movement mechanism 14 are operated so that the test tube S is moved to a position of B2 in FIG. 3. Then, in the test tube S, the cells attached to the inner surface of the test tube S and the liquid are separated. Then, the cells attached to the inner surface of the test tube S are detected by the color sensor 152.

At this time, since the liquid in the test tube S is turbid, the cells attached to the inner surface of the test tube S can be accurately detected by separating the cells attached to the inner surface and the liquid in the test tube S.

Then, the stirring processing is ended according to the discrimination that no cells are attached to the inner surface of the test tube S on the basis of the detection signal from the color sensor 152, so that the stirring processing can be ended at an appropriate timing.

Therefore, it is possible to reduce the work for determining the end of the stirring processing by the user.

As a result, the workability of the user when using the stirring device 11 can be improved.

(2) Further, in the present embodiment, in the stirring device 11, the holding mechanism 13 is operated to be rotated, so that the test tube S is moved to the position indicated by B2 of FIG. 3. In a state where the test tube S is located at B2, the lower end portion of the test tube S is located above, the upper end portion of the test tube is located below, and the test tube S is inclined with respect to the vertical direction. Then, due to gravity, the liquid is separated from the cells attached to the inner surface of the test tube S (liquid is moved downward).

Therefore, the cells attached to the inner surface of the test tube S and the liquid other than the cells can be separated with a simple configuration.

(3) In the present embodiment, in a case where the discrimination processor 191 discriminates that the cells are attached to the inner surface of the test tube S, the stirring processing is executed again in the stirring device 11.

Therefore, in the stirring device 11, the stirring processing can be automatically performed until the cells are not attached to the test tube S.

As a result, the workability of the user when using the stirring device 11 can be improved.

(4) Further, in the present embodiment, in the stirring device 11, the cell detection mechanism 15 includes the color sensor 152 that detects cells by color.

Therefore, the cells attached to the inner surface of the test tube S can be accurately detected by the cell detection mechanism 15.

(5) Further, in the present embodiment, the stirring device 11 is provided in the pre-processing apparatus 2.

Therefore, the workability of the user can be improved in the pre-processing apparatus 2.

5. Modification Example

In the above embodiment, the case where the mixed solution generated from the culture medium is stirred by the stirring device 11 has been described. However, the stirring device 11 can be used in a case of stirring any other liquid.

Further, in the above embodiment, it has been described that the cells attached to the test tube S are detected by the color sensor 152. However, the cells attached to the test tube S may be detected by other detection methods. For example, the cells attached to the test tube S may be detected by using a laser sensor. Further, the test tube S may be imaged with a camera, and the cells attached to the test tube S may be detected on the basis of the imaging result.

DESCRIPTION OF REFERENCE SIGNS 2 pre-processing apparatus
4 centrifugation mechanism
5 liquid removal mechanism
6 reagent supply mechanism
7 stirring mechanism
11 stirring device
13 holding mechanism
14 movement mechanism
15 cell detection mechanism
19 control unit
131 arm portion
132 main body portion
133 grip portion
141 up-down cylinder
142 main body portion
143 connection portion
144 rotation cylinder
145 cylinder body
146 gear
147 rotation portion
148 gear
149 bearing
151 support arm
152 color sensor
191 discrimination processor
192 operation processor

The invention claimed is:

1. A pre-processing apparatus for performing pre-processing on cells,
the pre-processing apparatus comprising:
a centrifugation mechanism that centrifuges a container in which a culture medium containing cells is housed;
a liquid removal mechanism that removes liquid other than the cells centrifuged in the container by the centrifugation mechanism;
a reagent supply mechanism that generates a mixed solution by mixing a reagent with the cells in the container after the liquid is removed by the liquid removal mechanism; and
a stirring device that stirs the mixed solution generated by the reagent supply mechanism, the stirring device comprising:
a stirring mechanism that stirs the mixed solution in a container in which the mixed solution is housed;
a solid-liquid separation mechanism that separates the cells attached to the container from liquid other than the cells in the container after the stirring by the stirring mechanism; and
a cell detection mechanism that detects whether or not the cells separated from the liquid by the solid-liquid separation mechanism are attached to the container,
wherein the solid-liquid separation mechanism rotates the container to separate the liquid other than the cells, from the cells attached to the container by gravity such that a lower end portion of the container is above an upper end portion of the container.

2. The pre-processing apparatus according to claim 1, further comprising:
a control unit that causes the stirring mechanism to execute the stirring again in a case where the cell detection mechanism detects that the cells are attached to the container.

3. The pre-processing apparatus according to claim 1, wherein the cell detection mechanism has a color sensor that detects the cells by color.

* * * * *